US012697141B2

(12) United States Patent
Munger et al.

(10) Patent No.: US 12,697,141 B2
(45) Date of Patent: Aug. 4, 2026

(54) FETAL VACUUM EXTRACTOR HAVING COMPACT, VERSATILE CONTROL HANDLE AND RELATED METHODS OF MANUFACTURE AND USE THEREOF

(71) Applicant: Laborie Medical Technologies Corp., Portsmouth, NH (US)

(72) Inventors: Jake Munger, Herriman, UT (US); Tomas Cartmill, Midvale, UT (US); Praveen Bollavaram, Saratoga Springs, UT (US); Aneesh Kuppam, South Jordan, UT (US)

(73) Assignee: Laborie Medical Technologies Corp., Portsmouth, NH (US)

( * ) Notice: Subject to any disclaimer, the term of this patent is extended or adjusted under 35 U.S.C. 154(b) by 0 days.

(21) Appl. No.: 18/505,852

(22) Filed: Nov. 9, 2023

(65) Prior Publication Data

US 2025/0152200 A1     May 15, 2025

(51) Int. Cl.
*A61B 17/44*          (2006.01)
*A61B 17/00*          (2006.01)

(52) U.S. Cl.
CPC .. *A61B 17/442* (2013.01); *A61B 2017/00526* (2013.01); *A61B 2017/00561* (2013.01);
(Continued)

(58) Field of Classification Search
CPC .............. A61B 17/2909; A61B 17/442; A61B 2017/2911; A61B 2017/306;
(Continued)

(56) References Cited

U.S. PATENT DOCUMENTS

| | | | |
|---|---|---|---|
| 2,194,989 | A | 3/1940 | Torpin |
| 2,702,038 | A | 2/1955 | Uddenberg et al. |

(Continued)

FOREIGN PATENT DOCUMENTS

| | | |
|---|---|---|
| CN | 113208711 A | 8/2021 |
| DE | 1123432 B | 2/1962 |

(Continued)

OTHER PUBLICATIONS

European Search Report for Application No. 24210757.1 dated Mar. 14, 2025, 13 pages.
(Continued)

*Primary Examiner* — Diane D Yabut
*Assistant Examiner* — Christian D Knauss
(74) *Attorney, Agent, or Firm* — TraskBritt

(57)          ABSTRACT

A vacuum extractor for use in childbirth includes a vacuum cup and a handle coupled to the vacuum cup. The handle includes a grip member and a pump member movably mounted on the grip member. The pump member is configured to be manually moved relative to the grip member by a user between a first position and a second position to generate a vacuum within the vacuum cup when the vacuum cup is disposed on the head of a fetus. The grip member includes a first laterally extending member and a second laterally extending member, which are separated from one another in a longitudinal direction. The user can grip either the first laterally extending member or the second laterally extending member while pushing the pump member toward the grip member to move the pump member from the first position to the second position during use of the vacuum extractor.

19 Claims, 8 Drawing Sheets

(52) U.S. Cl.
CPC ............... *A61B 2017/00681* (2013.01); *A61B 2017/00982* (2013.01)

(58) Field of Classification Search
CPC ........ A61B 2017/308; A61B 2017/445; A61B 2017/447
See application file for complete search history.

(56) References Cited

U.S. PATENT DOCUMENTS

| | | | |
|---|---|---|---|
| 2,917,050 | A | 12/1959 | Kenyon |
| 3,202,152 | A | 8/1965 | Wood et al. |
| 3,612,722 | A | 10/1971 | Neward |
| 3,765,408 | A | 10/1973 | Kawai |
| 5,019,086 | A | 5/1991 | Neward |
| 5,277,557 | A | 1/1994 | Cooper |
| 5,281,229 | A | 1/1994 | Neward |
| 5,693,058 | A | 12/1997 | Cavanagh et al. |
| 5,713,909 | A | 2/1998 | Lindsay |
| 5,803,926 | A | 9/1998 | Neward |
| 5,810,840 | A | 9/1998 | Lindsay |
| 5,935,136 | A | 8/1999 | Hulse et al. |
| 6,059,795 | A * | 5/2000 | Wallace ............... A61B 17/442 606/122 |
| 6,074,399 | A * | 6/2000 | Wallace ............... A61B 17/442 606/122 |
| 6,355,047 | B1 * | 3/2002 | Wallace ............... A61B 17/442 606/122 |
| 6,361,542 | B1 | 3/2002 | Dimitriu et al. |
| 6,468,284 | B1 * | 10/2002 | Wallace ............... A61B 17/442 606/122 |
| D873,990 | S * | 1/2020 | Dixon ......................... D24/108 |
| 2002/0165556 | A1 | 11/2002 | Wallace |

FOREIGN PATENT DOCUMENTS

| | | | |
|---|---|---|---|
| DE | 3138589 | A1 | 4/1983 |
| WO | 89/06112 | A1 | 7/1989 |

OTHER PUBLICATIONS

European Extended Search Report for Application No. 25196213.0 dated Nov. 12, 2025, 8 pages.

* cited by examiner

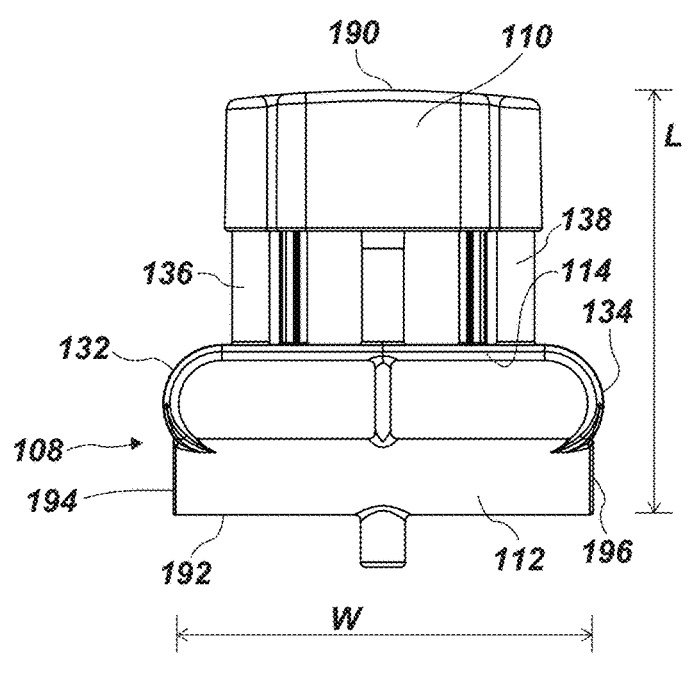
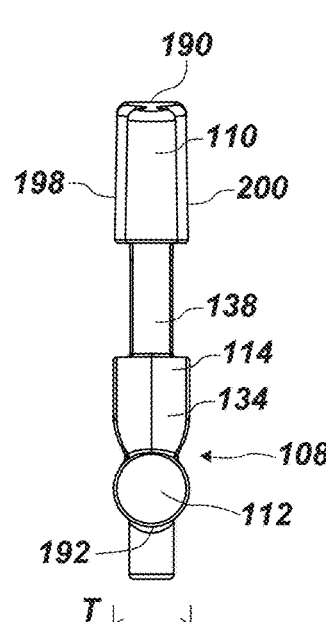
FIG. 7                 FIG. 8
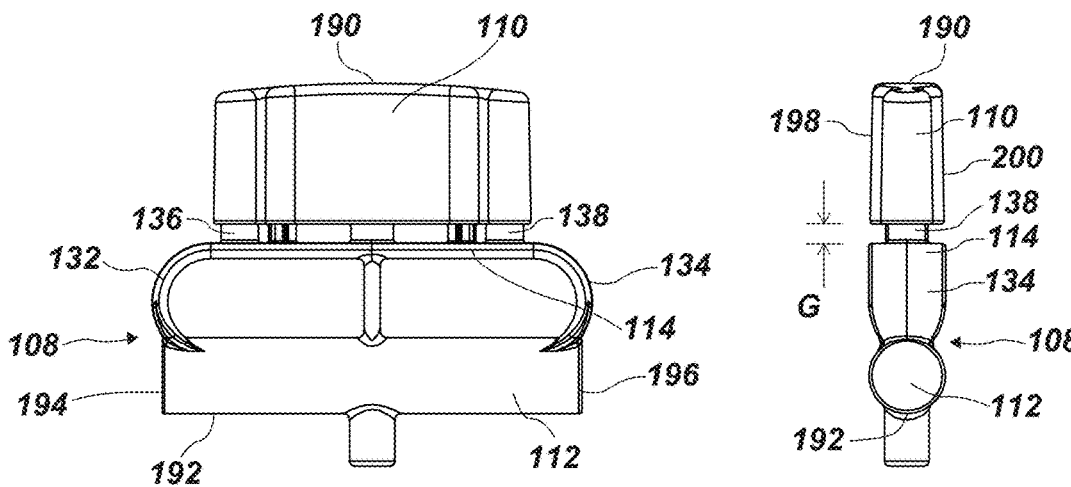
FIG. 9                 FIG. 10

FETAL VACUUM EXTRACTOR HAVING COMPACT, VERSATILE CONTROL HANDLE AND RELATED METHODS OF MANUFACTURE AND USE THEREOF

TECHNICAL FIELD

This disclosure relates generally to a fetal vacuum extractor device for extracting fetuses from the mother to facilitate delivery, and to methods of manufacturing and using such a fetal vacuum extractor.

BACKGROUND

During childbirth, the birth mother often requires assistance in the delivery of the fetus. In certain, more extreme instances, such assistance may include surgical intervention known as a Caesarean section delivery. A Caesarean delivery involves making an incision in the abdomen and uterus and extracting the fetus through the incisions. In less extreme cases, assistance is provided through the use of various extraction tools or instruments. Typically, such instruments include either forceps or a vacuum cup device, either of which is used to grip the head of the fetus and aid in maneuvering the fetus through the birth canal.

The use of forceps entails grasping and compressing the head of the fetus between a pair of opposable members at the distal end of a scissors-like instrument and then maneuvering the head of the fetus with the forceps. While the use of forceps allows for considerable manipulation of the fetus, the rigid instrument and force applied to the head by the gripping of the proximal ends of the forceps by the physician to maintain secure contact with the head of the fetus are potentially damaging to the soft and pliable head. The mother also may be inadvertently harmed during manipulation of the fetus due to the unyielding nature of the forceps.

Vacuum assisted extraction devices for performing Vacuum Assisted Deliveries (VADs) are well known alternatives to forceps. Vacuum assisted fetal extractors, sometimes referred to in their simplest manifestation as obstetric vacuum cups, may be utilized in order to apply an externally created vacuum force to the head of the fetus to secure the extractor to the head for use as a traction device. Vacuum cups generally operate by placing the cup on the head of the fetus, mechanically evacuating air from the cup and simultaneously drawing the cup against a portion of the head of the fetus. By so attaching the cup to the head, a traction force may be applied to the fetus such that it may be manipulated and the fetus pulled from the uterus in conjunction with the mother's contractions.

While vacuum assisted fetal extractors have provided many advantages in the delivery of a fetus from its mother, such devices also pose potential hazards if not properly utilized or adequately monitored during their use. Such hazards stem from the fact that the skull of the fetus is soft and structurally weak and thus renders the head of the fetus susceptible to deformation or injury during childbirth.

Misapplication or improper use of a vacuum assisted fetal extractor may result in any of a number of injuries to the fetus. Such injuries might include, by way of example only, subdural hematoma, subgaleal hemorrhage, chignon, abrasions, as well as other, less common injuries. While not an exhaustive list, injuries of the foregoing type listed above may be the result of improper placement of the vacuum cup on the head of the fetus, application of an excessive vacuum magnitude, application of an excessive traction magnitude, or maintaining a vacuum for an excessive continuous duration. Injury may also occur as a result of maintaining a vacuum for an excessive cumulative duration either during a specified period of time (e.g., longer than 20-30 minutes) or as a total cumulative duration.

In addition to the problems above, fetal vacuum extractors typically include a manual handle that is connected to the vacuum cup by a tube, which serves as a fluid conduit for generating the vacuum within the vacuum cup and as a cable through which the extraction force may be applied to the vacuum cup to assist in pulling the fetus from the uterus. The handle includes a pump mechanism, which is compressed repeatedly by the clinician to generate the vacuum, which takes time and effort on the part of the clinician who may be under stress and time constraints given the delivery complications encountered. Furthermore, due to variations in hand size on the part of the clinician, the handle may be too large or too small for any particular clinician. As a result, any particular handle design may be considered less than ideal from an ergonomic perspective by some clinicians with relatively larger or smaller hands.

After delivery, or occasionally during a delivery upon encountering complications, the vacuum within the vacuum cup must be released to allow the vacuum cup to be separated from the head of the fetus. Typically, the fetal vacuum extractor may include a mechanical button or other device on the handle that can be used to release the vacuum, but such mechanical buttons or devices frequently require use of the second hand of the clinician that is not holding the handle to actuate the button or device, which complicates the release of the vacuum.

BRIEF SUMMARY

In some embodiments, the present disclosure includes a vacuum extractor for use in childbirth that includes a vacuum cup and a handle coupled to the vacuum cup. The handle includes a grip member and a pump member movably mounted on the grip member. The pump member is configured to be manually moved relative to the grip member by a user between a first position and a second position. The movement of the pump member relative to the grip member between the first position and the second position generates a vacuum within the vacuum cup when the vacuum cup is disposed on the head of a fetus. The grip member includes a first laterally extending member and a second laterally extending member. The second laterally extending member is separated from the first laterally extending member in a longitudinal direction by a distance. Each of the first laterally extending member and the second laterally extending member are configured to be gripped by the fingers of a user while the pump member is disposed in the palm of the hand of the user, such that the user can grip either the first laterally extending member or the second laterally extending member while pushing the pump member toward the grip member to move the pump member from the first position to the second position during use of the vacuum extractor.

In some embodiments, the first laterally extending member may comprise a generally tubular structure defining a cavity therein, and the cavity is in fluid communication with an interior of the vacuum cup.

In some embodiments, the vacuum extractor further comprises a vacuum pressure indicator extending between an exterior of the grip member and the cavity within the first laterally extending member. The vacuum pressure indicator is configured to move relative to the first laterally extending member between a first position and a second position. The vacuum pressure indicator is biased to the first position by a biasing member. The vacuum pressure indicator is configured to gradually move from the first position toward the second position responsive to increasing vacuum pressure within the cavity. The position of the vacuum pressure indicator relative to the first laterally extending member provides a relative indication of an amount of vacuum pressure within the cavity.

In some embodiments, the vacuum pressure indicator and the first laterally extending member have cooperating features configured to release vacuum pressure within the cavity and the vacuum cup when the vacuum pressure indicator is in the second position relative to the first laterally extending member.

The vacuum pressure indicator may be manually moveable from the first position to the second position by a user, the vacuum pressure indicator thereby defining a vacuum pressure release mechanism for the vacuum extractor.

In some embodiments, the handle does not include any other vacuum release mechanism.

In some embodiments, an assembly of the grip member and the pump member has a maximum length of 105 mm or less between a proximal end surface of the pump member and a distal end surface of the first laterally extending member of the grip member, a maximum width between a first lateral side surface of the grip member and second lateral side surface of the grip member of 110 mm or less, and a maximum thickness between a front major surface and a rear major surface of the assembly of 20 mm or less.

In some embodiments, a vacuum pressure of at least −34.6 kPa relative to ambient pressure may be achieved within the vacuum cup after moving the pump member from the first position to the second position and then back to the first position five times or less while the vacuum cup is sealed.

In some embodiments, one of the grip member and the pump member has surfaces defining a fluid chamber, and the other of the grip member and the pump member has surfaces defining a piston disposed and moveable within the fluid chamber in response to movement of the pump member relative to the grip member between the first position and the second position.

In some embodiments, a volume within the fluid chamber may be reduced by at least 7.2 cm$^3$ upon movement of the pump member relative to the grip member between the first position and the second position.

In additional embodiments, the present disclosure includes a vacuum extractor for use in childbirth that includes a vacuum cup and a handle coupled to the vacuum cup. The handle includes a grip member and a pump member movably mounted on the grip member and configured to be manually moved relative to the grip member by a user between a first position and a second position. Movement of the pump member relative to the grip member between the first position and the second position generates a vacuum within the vacuum cup when the vacuum cup is disposed on the head of a fetus. An assembly of the grip member and the pump member has a maximum length of 105 mm or less between a proximal end surface of the pump member and a distal end surface of the first laterally extending member of the grip member, a maximum width between a first lateral side surface of the grip member and second lateral side surface of the grip member of 110 mm or less, and a maximum thickness between a front major surface and a rear major surface of the assembly of 20 mm or less. Furthermore, a vacuum pressure of at least −34.6 kPa relative to ambient pressure is achieved within the vacuum cup after moving the pump member from the first position to the second position and then back to the first position five times or less while the vacuum cup is sealed.

In additional embodiments, the present disclosure includes a vacuum extractor for use in childbirth that includes a vacuum cup and a handle coupled to the vacuum cup. The handle includes a grip member and a pump member movably mounted on the grip member and configured to be manually moved by a user relative to the grip member between a first position and a second position. Movement of the pump member relative to the grip member between the first position and the second position generates a vacuum within the vacuum cup when the vacuum cup is disposed on the head of a fetus. One of the grip member and the pump member has surfaces defining a fluid chamber, and another of the grip member and the pump member has surfaces defining a piston disposed and moveable within the fluid chamber in response to movement of the pump member relative to the grip member between the first position and the second position. An assembly of the grip member and the pump member has a maximum length of 105 mm or less between a proximal end surface of the pump member and a distal end surface of the first laterally extending member of the grip member, a maximum width between a first lateral side surface of the grip member and second lateral side surface of the grip member of 110 mm or less, and a maximum thickness between a front major surface and a rear major surface of the assembly of 20 mm or less. Furthermore, a volume within the fluid chamber is reduced by at least 7.2 cm$^3$ upon movement of the pump member relative to the grip member between the first position and the second position.

Additional embodiments of the present disclosure include methods of forming fetal vacuum extractors as described herein. For example, a method of forming a vacuum extractor for use in childbirth may involve providing a vacuum cup, and forming a grip member including a first laterally extending member and a second laterally extending member, the second laterally extending member separated from the first laterally extending member in a longitudinal direction by a distance, wherein each of the first laterally extending member and the second laterally extending member are configured to be gripped by the fingers of a user. The method may include forming a handle by moveably mounting a pump member to the grip member and configuring the pump member to be manually movable relative to the grip member by a user between a first position and a second position. The vacuum cup may be coupled to the handle with a fluid conduit. The grip member and the pump member may be configured such that movement of the pump member relative to the grip member between the first position and the second position generates a vacuum within the vacuum cup when the vacuum cup is disposed on the head of a fetus, and such that the user can grip either the first laterally extending member or the second laterally extending member while pushing the pump member toward the grip member to move the pump member from the first position to the second position during use of the vacuum extractor.

BRIEF DESCRIPTION OF THE DRAWINGS

For a detailed understanding of the present disclosure, reference should be made to the following detailed description, taken in conjunction with the accompanying drawings, in which like elements have generally been designated with like numerals, and wherein:

FIG. 7 is a front view of the handle of the vacuum extractor shown in FIG. 1, the handle including a grip member and a pump member moveable relative to the grip member, the pump member shown in an uncompressed first position relative to the grip member;

FIG. 8 is a side view of the handle shown in FIG. 7;

FIG. 9 is a front view of the handle of the vacuum extractor shown in FIG. 1 illustrating the pump member in a compressed second position relative to the grip member;

FIG. 10 is a side view of the handle shown in FIG. 9;

DETAILED DESCRIPTION

Figure 1:
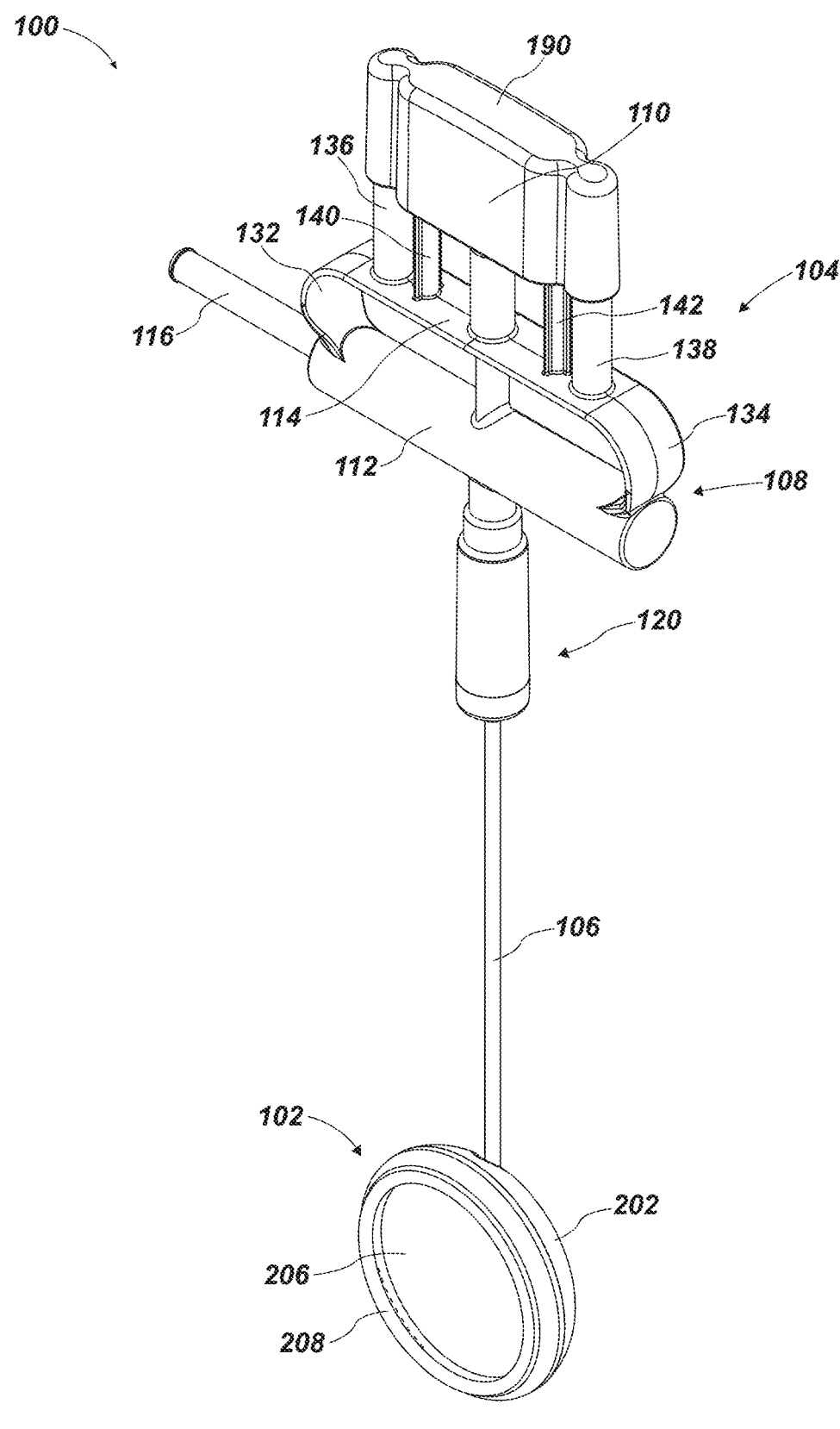
FIG. 1 is a perspective view of a vacuum extractor for use in childbirth in accordance with an embodiment of the present disclosure.

The illustrations presented herein are not actual views of any particular fetal vacuum extractor, or any component thereof, but are merely idealized representations, which are employed to describe embodiments of the present disclosure.

As used herein, the singular forms following "a," "an," and "the" are intended to include the plural forms as well, unless the context clearly indicates otherwise.

As used herein, the term "may" with respect to a material, structure, feature, or method act indicates that such is contemplated for use in implementation of an embodiment of the disclosure, and such term is used in preference to the more restrictive term "is" so as to avoid any implication that other compatible materials, structures, features, and methods usable in combination therewith should or must be excluded.

As used herein, any relational term, such as "first," "second," "top," "bottom," "upper," "lower," "above," "beneath," "side," "upward," "downward," etc., is used for clarity and convenience in understanding the disclosure and accompanying drawings, and does not connote or depend on any specific preference or order, except where the context clearly indicates otherwise. For example, these terms may refer to an orientation of elements of any fetal vacuum extractor when utilized in a conventional manner. Furthermore, these terms may refer to an orientation of elements of any fetal vacuum extractor as illustrated in the drawings.

As used herein, the term "substantially" in reference to a given parameter, property, or condition means and includes to a degree that one skilled in the art would understand that the given parameter, property, or condition is met with a small degree of variance, such as within acceptable manufacturing tolerances. By way of example, depending on the particular parameter, property, or condition that is substantially met, the parameter, property, or condition may be at least 90.0% met, at least 95.0% met, at least 99.0% met, or even at least 99.9% met.

As used herein, the term "about" used in reference to a given parameter is inclusive of the stated value and has the meaning dictated by the context (e.g., it includes the degree of error associated with measurement of the given parameter, as well as variations resulting from manufacturing tolerances, etc.).

Figure 2:
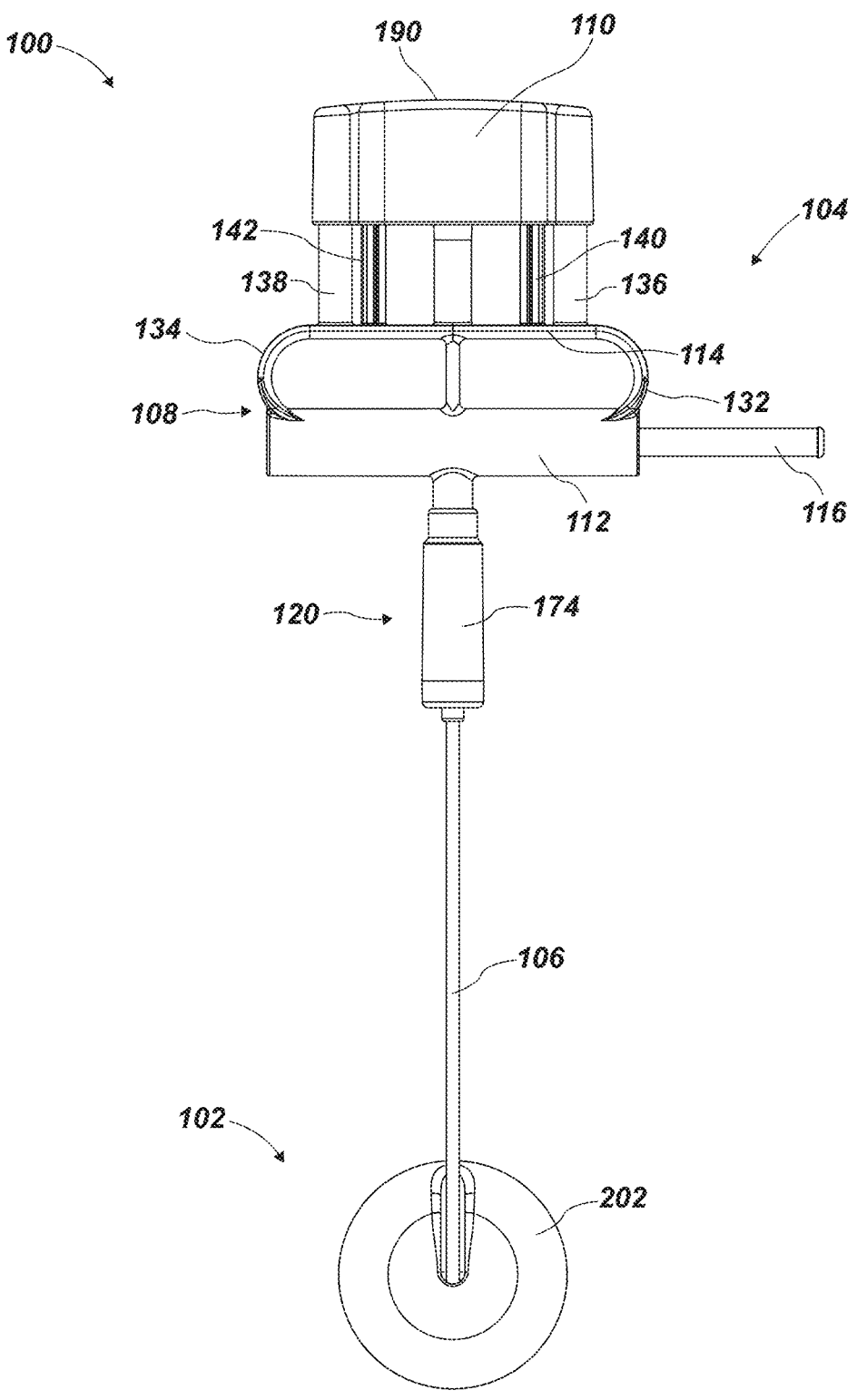
FIG. 2 is a front view of the vacuum extractor shown in FIG. 1.

FIG. 1 is a perspective view of a fetal vacuum extractor 100 for use in childbirth, and FIG. 2 is a front view of the fetal vacuum extractor 100 in accordance with embodiments of the present disclosure. As shown in FIGS. 1 and 2, the fetal vacuum extractor 100 includes a vacuum cup 102 and a handle 104 coupled to the vacuum cup 102 by a fluid (e.g., air or gas) conduit 106.

The handle 104 includes a grip member 108 and a pump member 110. The pump member 110 is movably mounted on the grip member 108 and configured to be manually moved relative to the grip member 108 by the hand of the user (e.g., clinician) between a first position and a second position. Movement of the pump member 110 relative to the grip member 108 between the first position and the second position generates a vacuum within the vacuum cup 102 when the vacuum cup 102 is disposed on the head of a fetus, as discussed in further detail hereinbelow.

The grip member 108 includes a first laterally extending member 112 and a second laterally extending member 114. The second laterally extending member 114 is separated from the first laterally extending member 112 in a longitudinal direction by a distance D1, which may be in a range from about 15 mm to about 30 mm, for example. Each of the first laterally extending member 112 and the second laterally extending member 114 are configured to be gripped by the fingers of the user while the pump member 110 is disposed in the palm of the hand of the user, such that the user can grip either the first laterally extending member 112 or the second laterally extending member 114 while pushing the pump member 110 toward the grip member 108 to move the pump member 110 from the uncompressed first position to the compressed second position during use of the vacuum extractor 100.

The fetal vacuum extractor 100 may also include a vacuum pressure indicator 116 that may be used to indicate a level of pressure, either quantitatively (calibrated value of pressure in units of vacuum pressure) or qualitatively (low pressure, medium pressure, high pressure, etc.), which may be used to indicate to the user that the vacuum pressure in the vacuum cup 102 is either too low or too high, for example.

The fetal vacuum extractor 100 may also include a traction force indicator 120 between the fluid conduit 106 and the handle 104. As the clinician applies tension to the fluid conduit during delivery by pulling on the handle 104, the traction force indicator 120 may be used to indicate a level of traction force, either quantitatively (calibrated value of tensile force) or qualitatively (low force, medium force, high force, etc.), which may be used to indicate to the user that the traction force is too high, for example, so as to avoid injury to the fetus.

Figure 3:
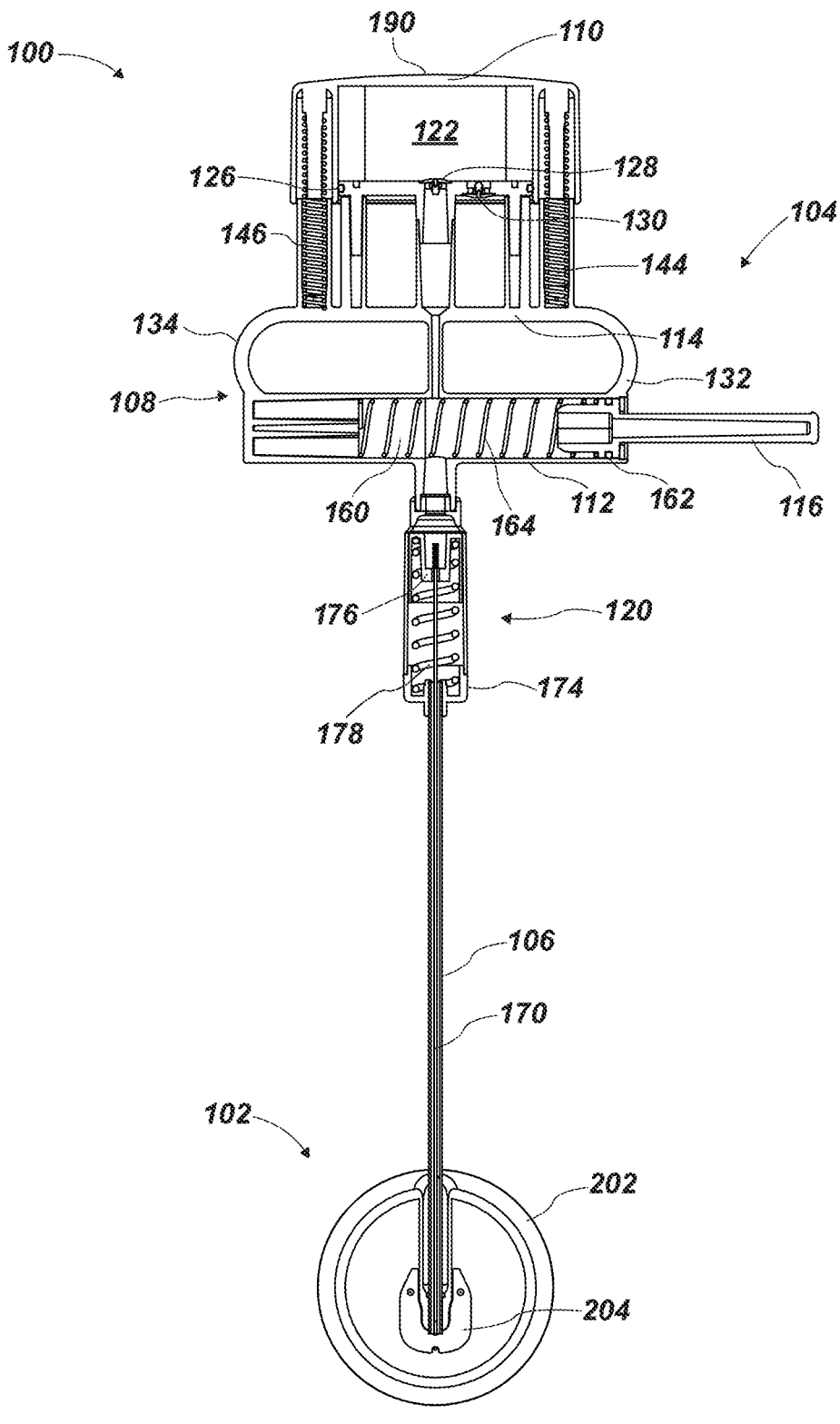
FIG. 3 is a cross-sectional view of the vacuum extractor shown in FIG. 1.

FIG. 3 is a cross-sectional view of the fetal vacuum extractor 100. The handle 104 comprises a pump mechanism that can be actuated by the user to generate a vacuum pressure (a negative pressure relative to the ambient pressure outside the fetal vacuum extractor 100). To this end, one of the grip member 108 and the pump member 110 has surfaces defining a fluid chamber 122 within the handle 104, and the other of the grip member 108 and the pump member 110 has surfaces defining a piston 124 disposed and moveable within the fluid chamber 122 in response to movement of the pump member 110 relative to the grip member 108 between a first position and a second position. In the embodiment illustrated in the figures, the pump member 110 has internal surfaces defining the fluid chamber 122, and the grip member 108 has surfaces defining the piston 124. In additional embodiments, however, the pump member 110 may comprise the piston and the grip member 108 may comprise the fluid chamber 122.

Figure 4:
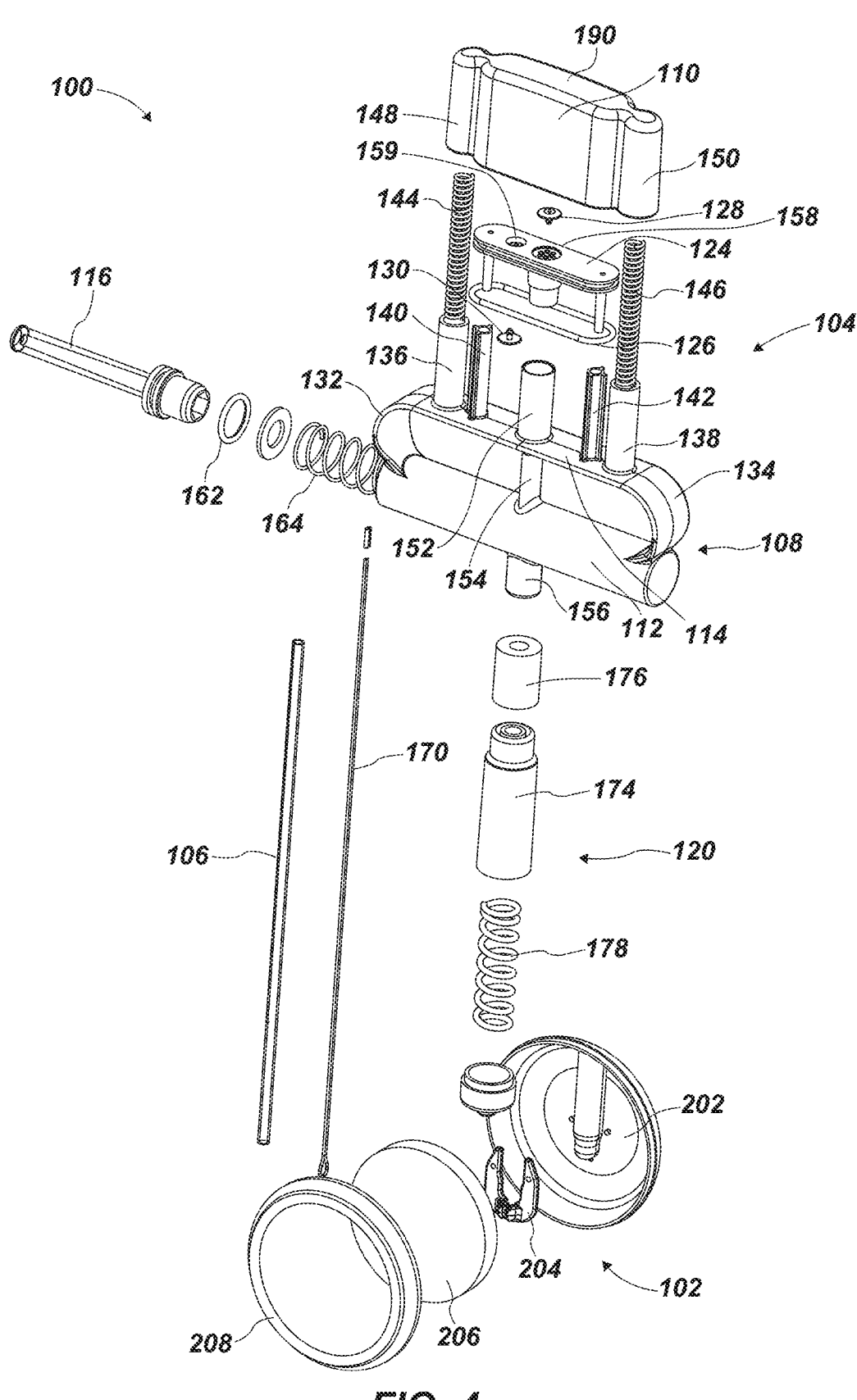
FIG. 4 is an exploded view of the vacuum extractor shown in FIG. 1 illustrating various components thereof.

As best illustrated in FIG. 4, the grip member 108 may comprise an assembly of components including a main body 126, the piston 124, a sealing member 126, a first one-way fluid valve 128, and a second one-way fluid valve 130.

The second laterally extending member 114 is generally planar and extends laterally between two end portions 132, 134 that each extends to is connected with the first laterally extending member 112 so as to define a space between the first laterally extending member 112 and the second laterally extending member 114 into which the user may extend the fingers of one hand when gripping the handle 104. In this case, the user grips the handle 104 with the pump member 110 in the palm of the hand and the fingers grip the underside of the second laterally extending member 114. Thus, the space between the first laterally extending member 112 and the second laterally extending member 114 should be large enough to accommodate insertion of the fingers of the user therein. Alternatively, the user may grip the handle 104 with the pump member 110 in the palm of the hand and the fingers gripping the underside of the first laterally extending member 112. Thus, the handle 104 can accommodate different users having relatively larger or smaller hands in a comfortable manner.

The handle 104 further comprises two hollow, cylindrical guide posts 136, 138 that extend upwardly from the upper surface of the second laterally extending member 114. Springs 144, 146 are disposed within the guide posts 136, 138. The pump member 110 includes complementary receptacles 148, 150 that are sized and shaped to receive the springs 144, 146 and guide posts 136, 138 therein. The springs 144, 146 bias the pump member 110 to a position remote from the grip member 108. As the handle 104 is compressed by the grip of a user, the pump member 110 can be pushed toward the grip member 108 against the biasing force of the springs 144, 146 with the guide posts 136, 138 sliding into the complementary receptacles 148, 150 in the pump member 110. Features such as protrusions and/or recesses may be formed inside the receptacles 148, 150 and inside the guide posts 136, 138 that mechanically interfere and interlock with the springs 144, 146 so as to mechanically retain the pump member 110 on the grip member 108.

The handle 104 further comprises two piston support posts 140, 142 that support the piston 124 thereon. In the embodiment shown in the figures, the piston support posts 140, 142 include recesses in the ends thereof, and the piston 124 has two complementary protrusions 152, 154 that extend into the recesses in the ends of the piston support posts 140, 142. The protrusions 152, 154 may be permanently secured within the recesses using, for example, an adhesive, ultrasonic welding, or solvent welding. In other embodiments, the piston 124 could be integrally formed with the grip member 108.

The piston 124 has a groove or recess in a peripheral side surface thereof, in which is positioned the sealing member

126. The sealing member 126 may comprise an elastomeric annular member (such as an O-ring) that has a complementary shape to the recess in the peripheral side surface of the piston 124. The sealing member 126 ensures a fluid-tight seal is established between the peripheral side surface of the piston 124 and the interior side walls of the pump member 110 that define the fluid chamber 122 therein.

The grip member 108 further includes a first tube member 152, a second tube member 154, and a third tube member 156, each of which is hollow so as to define a fluid passageway therein. The first tube member 152 extends upwardly from the second laterally extending member and cooperates with an aperture extending through a center of the piston 124 in which is positioned the first one-way valve 128. The second tube member 154 extends between a central region of the first laterally extending member 112 and the second laterally extending member 114. The third tube member 156 extends downward, or distally, from the center of the first laterally extending member 112 and is fluidly connected to the fluid conduit 106. Thus, fluid communication is established between the vacuum cup 102 and the fluid chamber 122 in the pump member 110 through the first, second, and third tube members 152, 154, 156.

The first one-way valve 128 is positioned in a first aperture 158 in a central region of the piston 124 and is configured such that fluid can only enter into the fluid chamber 122 through the first one-way valve 128, but fluid cannot be expelled out from the fluid chamber 122 through the first one-way valve 128. The piston 124 further comprises a second aperture 159 extending through the piston 124 in which is positioned the second one-way valve 130. The second one-way valve 130 is positioned in the second aperture 159 in the piston 124, and is configured such that fluid can only exit from the fluid chamber 122 through the second one-way valve 130 to the ambient atmosphere external to the handle 104, but fluid cannot enter into the fluid chamber 122 through the second one-way valve 130.

Figure 5:
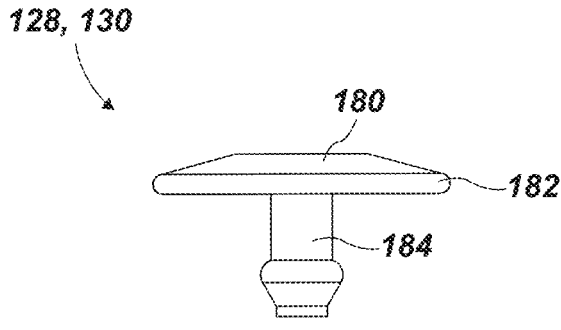
FIG. 5 is a side view of a one-way umbrella valve of the vacuum extractor shown in FIG. 1.
Figure 6:
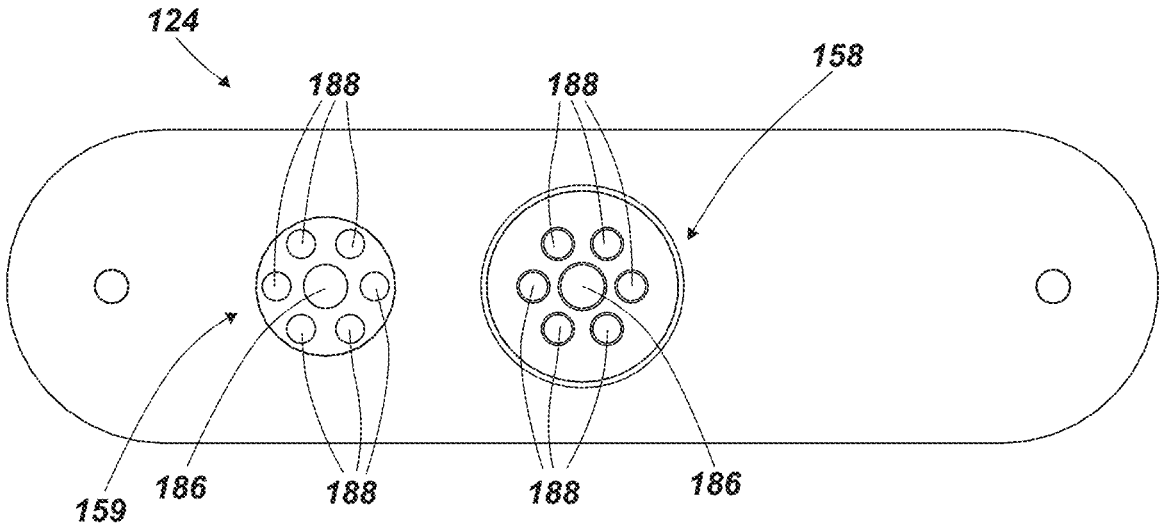
FIG. 6 is a top view of a piston of the one-way umbrella valve of the vacuum extractor shown in FIG. 1.

Referring to FIG. 5, each of the first one-way valve 128 and the second one-way valve 130 may comprise, for example, a so-called umbrella valve 180 including an elastomeric flap member 182 and an integral post member 184 extending therefrom. Referring to FIG. 6, the post member 184 is secured within a post hole 186 in the piston 124 such that the flap member 182 rests against the surface of the piston 124 over one or more vent holes 188 formed through the piston 124. The vent hole(s) 188 forms the aperture(s) 158, 159 through which fluid flows through the piston 124. Due to the elastomeric nature of the umbrella valve 180, fluid pressure will push the flap member 182 against the vent holes 188 in a sealing manner to prevent fluid from flowing through the vent holes 188 in one direction, but a vacuum pressure will allow fluid to flow through the vent holes 188 in the opposite second direction. Any other type of one-way valve may also be used in additional embodiments of the present disclosure.

Referring again to FIG. 3, the first laterally extending member 112 comprises a generally tubular structure defining a cavity 160 therein. The cavity 160 is in fluid communication with the interior of the vacuum cup 102 by way of the third tube member 156 and the fluid conduit 106, and is in fluid communication with the fluid chamber 122 by way of the second tube member 154, the third tube member 156, and the first aperture in the piston in which the first one-way valve 128 is positioned.

The cavity 160 in the first laterally extending member 112 is generally cylindrical. The vacuum pressure indicator 116 is elongated and extends from the cavity 160 within the first laterally extending member 112 laterally to the exterior of the grip member 108. The vacuum pressure indicator 116 is configured to move relative to the first laterally extending member 112, by sliding within the first laterally extending member 112, between a first position and a second position. The vacuum pressure indicator 116 thus takes the form of a piston configured to slide within a cylinder formed by interior surfaces of the first laterally extending member 112 that define the cavity 160 therein.

As shown in FIG. 4, an enlarged portion of the vacuum pressure indicator 116 has a groove or recess in a peripheral side surface thereof, in which is positioned a sealing member 162. The sealing member 162 may comprise an elastomeric annular member (such as an O-ring) that has a complementary shape to the recess in the peripheral side surface of the vacuum pressure indicator 116. The sealing member 162 ensures a fluid-tight seal is established between the peripheral side surface of the vacuum pressure indicator 116 and the interior surfaces of the first laterally extending member 112 that define the cavity 160 therein.

The vacuum pressure indicator 116 is biased to a first extended position by a biasing member in the form of a spring 164. The vacuum pressure indicator 116 is configured to gradually move from the first extended position toward a retracted second position within the first laterally extending member 112 responsive to increasing vacuum pressure (decreasing pressure) within the cavity 160. The position of the vacuum pressure indicator 116 relative to the first laterally extending member 112 thus provides the user with a relative indication of an amount of vacuum pressure within the cavity 160 and, hence, the vacuum cup 102.

The vacuum pressure indicator 116 and the first laterally extending member 112 may have cooperating features configured to release vacuum pressure within the cavity 160 and the vacuum cup 102 when the vacuum pressure indicator 116 is in the retracted second position relative to the first laterally extending member 112. For example, referring to FIG. 3, as the vacuum pressure indicator 116 is drawn or forced into the first laterally extending member 112, a position will be reached at which the sealing member 162 on the vacuum pressure indicator 116 will pass the fluid passageway in the third tube member 156, which will then allow fluid to flow between the vacuum pressure indicator and the interior surfaces of the first laterally extending member 112 in the cavity 160 and into fluid conduit 106 and the vacuum cup 102, thereby releasing the vacuum pressure therein.

The vacuum pressure indicator 116 may be manually moveable from the first extended position to the second retracted position by a user, the vacuum pressure indicator 116 thereby defining a vacuum pressure release mechanism for the fetal vacuum extractor 100. In some embodiments, the handle 104 may not include any other vacuum release mechanism, which may simplify use of the fetal vacuum extractor 100 and simplify operation of the vacuum extractor 100 for the user.

The fluid conduit 106 may be formed of an extruded polymer (e.g., a plastic or elastomeric) material. In some embodiments, one or more cables 170 may extend through the fluid passageway with one end thereof fastened to the handle 104 and the other end thereof fastened to the vacuum cup 102. The cable 170 is formed of a material, such as a metal or a metal alloy, exhibiting a higher elastic modulus than that exhibited by the material forming the fluid conduit 106. The cable 170 allows the user to pull on the handle 104 while the vacuum cup 102 is secured with vacuum pressure therein to the head of a fetus. The cable 170 carries at least a majority of the tensile forces applied during use so as to prevent damage or deformation of the fluid conduit 106 by the tensile forces.

The traction force indicator 120 is secured to the distal end of the third tube member 156 of the grip member 108. The traction force indicator 120 includes a cylindrical tubular member 174 and an anchor member 176 configured to slide within the tubular member 174. A biasing member in the form of a spring 178 is disposed within the tubular member 174 and pushes the anchor member 176 toward the grip member 108. One end of the cable 170 is attached to the anchor member 176. The anchor member 176 is configured to allow fluid to flow through the tubular member 174 past the anchor member 176 in either the proximal direction (the direction extending from the vacuum cup 102 toward the handle 104) or the distal direction (the direction extending from the handle 104 toward the vacuum cup 102).

As tension is applied to the cable 170 during use, the cable 170 will pull the anchor member 176 in the downward, distal direction against the spring force of the spring 178. At least a portion of the tubular member 174 may be optically transparent, such that the user can see the position of the anchor member 176 through the tubular member 174. Markings may be applied to the exterior surface of the tubular member to indicate a level of traction force achieved as a function of the position of the anchor member 176 within the tubular member 174 relative to the markings on the exterior surface of the tubular member 174.

In some embodiments, the traction force indicator 120 may further be configured to function as a safety release mechanism. In such an embodiment, as the clinician applies tension to the fluid conduit during delivery by pulling on the handle 104, if the tension force exceeds a predetermined level, the traction force indicator 120 may automatically release the vacuum in the vacuum cup 102 and/or mechanically release (or prevent further increase of) the tension in the fluid conduit 106 so as to avoid injury to the fetus. An aperture may be formed through a sidewall of the tubular member 174 at or proximate a lower end thereof, and a fluid-tight seal may be provided between the outer diameter of the anchor member 176 and the interior sidewall of the tubular member 174 (using, for example, one or more O-rings) while the spring 178 holds the anchor member 176 in the upward, proximal position. The anchor member 176 may be further configured such that, after the anchor member 176 moves a predetermined distance in the downward, distal direction against the biasing force of the spring 178 (due to tensile force applied to the cable 170 by pulling on the handle 104), the aperture in the sidewall of the tubular member 174 will be uncovered, allowing fluid to flow from the exterior of the tubular member 174 into the fluid conduit 106 and the vacuum cup 102, thereby releasing the vacuum therein. Alternatively, rather than forming an aperture through the sidewall of the tubular member 174, a groove or recess could be formed in the interior sidewall of the tubular member so as to provide a fluid pathway through the groove or recess to the exterior ambient once the fluid-tight seal between the tubular member 174 and the anchor member 176 reaches the groove or recess. Thus, upon applying excessive tensile forces to the cable 170, the vacuum will be released, which will release the vacuum cup 102 from the head of the fetus, thereby preventing damage to the fetus.

Referring again to FIG. 4, the vacuum cup 102 may include a cup housing 202, a cable anchor 204, an insert 206, and a sealing ring 208 configured to couple to the cup housing 202. The cup housing 202 comprises a conduit coupling feature that is connected to the fluid conduit 106 in a fluid-tight member in a manner establishing fluid communication between the fluid conduit 106 and the interior of the vacuum cup 102. The cable anchor 204 is coupled to an end of the cable 170 that extends through the fluid conduit 106 to the interior of the vacuum cup 102. The insert 206 is used to prevent or hinder the ingress of liquids or other non-gaseous matter into the fluid conduit 106. The insert 206 may comprise an open cell foam material or a volume of fibrous material. In other embodiments, the insert 206 may comprise a closed cell foam material or a volume of solid light-weight fluid impermeable material that has been punctured one or more times to form a limited number of fluid paths through the insert 206. By employing such a closed cell foam material or a volume of solid light-weight fluid impermeable material that has been punctured one or more times, the fluid volume within the vacuum cup 102 may be reduced or minimized, which may increase the vacuum pressure that may be achieved within the vacuum cup 102 with each pump cycle. The sealing ring 208 and the cup housing 202 each may be formed of a relatively rigid plastic material. The sealing ring 208 may be coupled to the cup housing 202 using an adhesive, ultrasonic welding, solvent welding, or mechanical interference, for example, but the joint between the sealing ring 208 and the cup housing 202 should be airtight.

FIGS. 7 and 8 are front and side views, respectively, of an assembly comprising the grip member 108 and the pump member 110, with the pump member 110 in the first uncompressed position, and FIGS. 9 and 10 are front and side views, respectively, of the assembly, with the pump member 110 in the second compressed position. Each pumping cycle involves moving the pump member 110 from the first uncompressed position shown in FIGS. 7 and 8 to the second compressed position shown in FIGS. 9 and 10, and then allowing the springs 144, 146 (FIGS. 3 and 4) to return the pump member 110 to the first uncompressed position shown in FIGS. 7 and 8. The springs 144, 146 may have a spring rate of, for example, between about 11 pounds per inch of travel and about 15 pounds per inch of travel (e.g., 16 pounds per inch of travel).

As shown in FIGS. 7 and 8, the assembly of the grip member 108 and the pump member 110 has a maximum length L of 105 mm or less between a proximal end surface 190 of the pump member 110 and a distal surface 192 of the first laterally extending member 112 of the grip member 108, a maximum width W between a first lateral side surface 194 of the grip member 108 and second lateral side surface 196 of the grip member 108 of 110 mm or less, and a maximum thickness T between a front major surface 198 and a rear major surface 200 of the assembly of 20 mm or less.

As shown in FIGS. 9 and 10, the handle 104 may be configured such that, when the pump member 110 is in the second compressed position shown in FIGS. 9 and 10, a gap G is present between the upper surface of the second laterally extending member 114 and the lower surface of the pump member 110. By way of example, the gap G may be greater than or equal to 4 mm, such as in a range of from 4 mm to 10 mm, more particularly between about 4 mm and 6 mm (e.g., about 4.5 mm). The gap G may prevent or avoid pinching of the fingers of the user between the upper surface of the second laterally extending member 114 and the lower surface of the pump member 110 during use of the fetal vacuum extractor 100.

Figure 11:
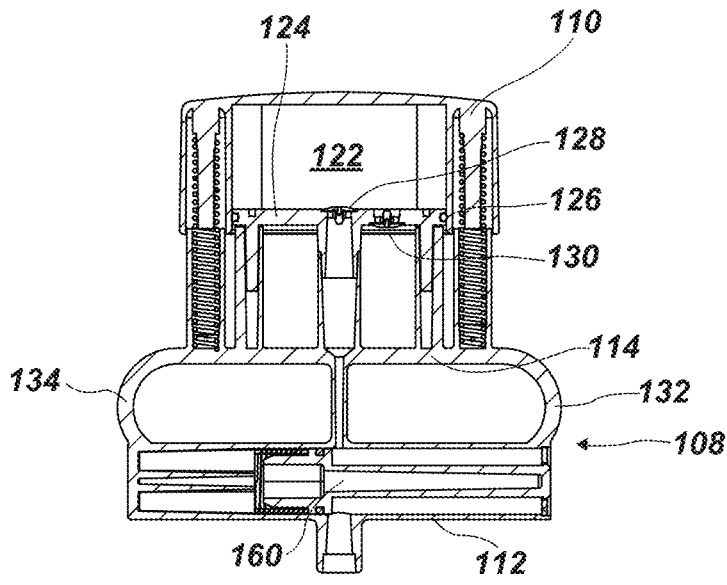
FIG. 11 is a cross-sectional view of the handle shown in FIG. 7 illustrating the pump member in the uncompressed first position relative to the grip member.
Figure 12:
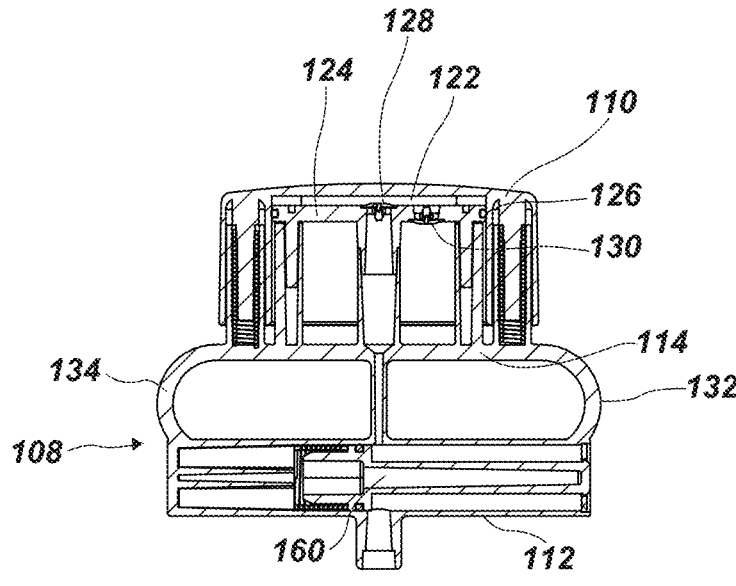
FIG. 12 is a cross-sectional view of the handle shown in FIG. 9 illustrating the pump member in the compressed second position relative to the grip member.

FIGS. 11 and 12 are cross-sectional views of the assembly of the grip member 108 and the pump member 110, with FIG. 11 showing the pump member 110 in the first uncompressed position, and FIG. 12 showing the pump member 110 in the second compressed position. The volume within the fluid chamber 122 may be reduced by at least 7.2 cm³ upon movement of the pump member 110 relative to the grip member 108 between the first position shown in FIG. 11 and the second position shown in FIG. 12.

During use of the fetal vacuum extractor 100, the user will insert the vacuum cup 102 into the vagina of the mother and position the vacuum cup 102 into position on the head of the fetus and will hold the vacuum cup 102 with one hand. The user will then pump the handle using the other hand. With each pump, the user will move the piston member 110 from the first position to the second position, during which fluid in the fluid chamber 122 will pass through the second one-way valve 130 to the environment exterior to the handle 104. The springs 144, 146 then force the pump member 110 back to the first position. As the pump member 110 moves back to the first position, fluid is drawn from the interior of the vacuum cup 102, through the fluid conduit 106, through the grip member 108, and through the first one-way valve 128 into the fluid chamber 122, thereby creating a vacuum pressure within the vacuum cup 102 (a negative pressure difference between the pressure inside the vacuum cup 102 and the ambient pressure outside the fetal vacuum extractor 100). The vacuum pressure inside the cavity 160 in the first laterally extending member 112 will cause the ambient pressure outside the handle 104 to push the vacuum pressure indicator into the first laterally extending member 112 against the biasing force of the spring 164. With each pump cycle, the vacuum pressure within the vacuum cup 102 will increase (an increasing magnitude of the negative pressure differential), and the vacuum pressure indicator 116 will move further inside the first laterally extending member 112. Once sufficient vacuum pressure has been established, the user may then pull the handle 104 away from the mother so as to apply a tensile force to the fluid conduit 106 (or to the cable 170 within the fluid conduit 106) to assist in delivery of the fetus. After delivery or in the event the vacuum cup 102 needs to be released from the head of the fetus for any reason, the user may press the vacuum pressure indicator 116 further into the first laterally extending member 112 to release the vacuum pressure and remove the vacuum cup 102 as previously discussed.

Figure 13:
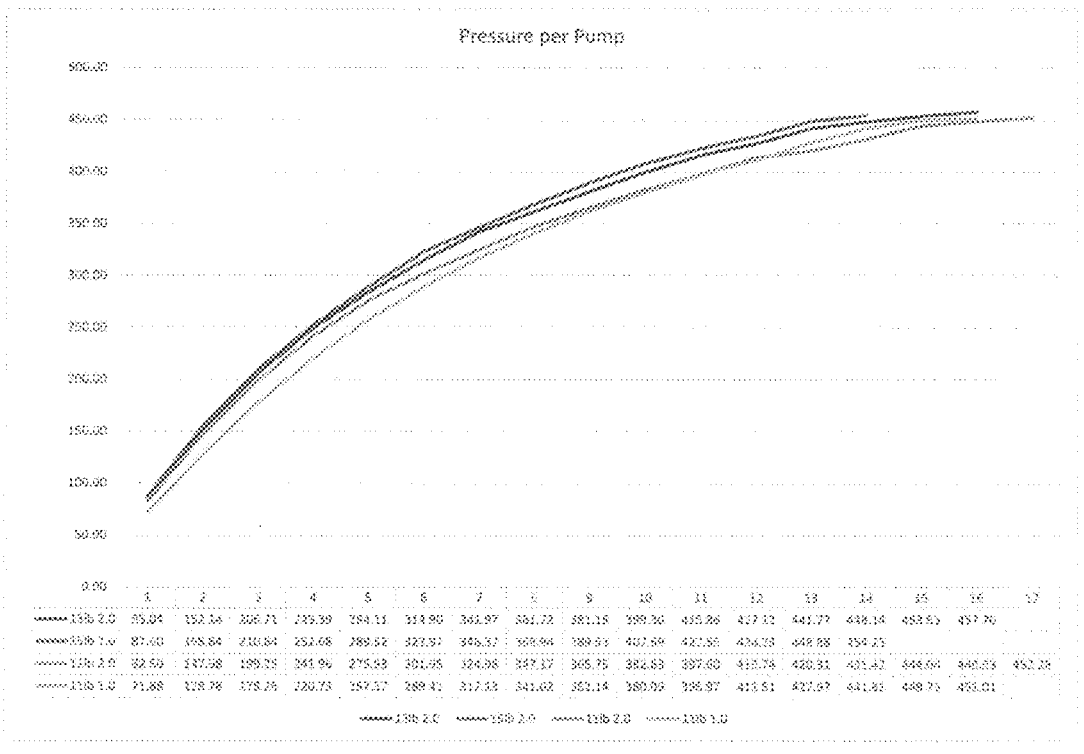
FIG. 13 is a graph illustrating a vacuum pressure within the vacuum cup of the vacuum extractor shown in FIG. 1 as a function of the number of pumps of the pump member of the vacuum extractor.

FIG. 13 is a graph illustrating the vacuum pressure that may be achieved within the vacuum cup 102 as a function of the number of pump cycles performed using the handle 104 for an embodiment of the fetal vacuum extractor 100 in accordance with the present disclosure, and for a previously known and commercially available fetal vacuum extractor. As can be seen in FIG. 13, a vacuum pressure of at least −34.6 kPa relative to ambient pressure may be achieved within the vacuum cup 102 after moving the pump member 110 from the first position to the second position and then back to the first position five times or less while the vacuum cup is sealed. The previously known fetal vacuum extractor requires more pumps to achieve the same vacuum pressure within the vacuum cup. This is due, at least in part, to the dimensions of the fluid chamber 122, the cavity 160, and the vacuum cup 102, and to other aspects of the configuration of the handle 104, all of which are achieved while maintaining an ergonomic design that can be comfortably used by persons with relatively larger or smaller hands.

Non-limiting example embodiments of the present disclosure may include:

Embodiment 1: A vacuum extractor for use in childbirth, comprising: a vacuum cup; a handle coupled to the vacuum cup, the handle including: a grip member; and a pump member movably mounted on the grip member and configured to be manually moved relative to the grip member by a user between a first position and a second position, movement of the pump member relative to the grip member between the first position and the second position generating a vacuum within the vacuum cup when the vacuum cup is disposed on the head of a fetus; wherein the grip member includes a first laterally extending member and a second laterally extending member, the second laterally extending member separated from the first laterally extending member in a longitudinal direction by a distance, wherein each of the first laterally extending member and the second laterally extending member are configured to be gripped by the fingers of a user while the pump member is disposed in the palm of the hand of the user, such that the user can grip either the first laterally extending member or the second laterally extending member while pushing the pump member toward the grip member to move the pump member from the first position to the second position during use of the vacuum extractor.

Embodiment 2: The vacuum extractor of Embodiment 1, wherein the first laterally extending member comprises a generally tubular structure defining a cavity therein, the cavity in fluid communication with an interior of the vacuum cup.

Embodiment 3: The vacuum extractor of Embodiment 2, further comprising a vacuum pressure indicator extending between an exterior of the grip member and the cavity within the first laterally extending member, the vacuum pressure indicator configured to move relative to the first laterally extending member between a first position and a second position, the vacuum pressure indicator being biased to the first position by a biasing member, and wherein the vacuum pressure indicator is configured to gradually move from the first position toward the second position responsive to increasing vacuum pressure within the cavity, the position of the vacuum pressure indicator relative to the first laterally extending member providing a relative indication of an amount of vacuum pressure within the cavity.

Embodiment 4: The vacuum extractor of Embodiment 3, wherein the vacuum pressure indicator and the first laterally extending member have cooperating features configured to release vacuum pressure within the cavity and the vacuum cup when the vacuum pressure indicator is in the second position relative the first laterally extending member.

Embodiment 5: The vacuum extractor of Embodiment 3 or Embodiment 4, wherein the vacuum pressure indicator is manually moveable from the first position to the second position by a user, the vacuum pressure indicator thereby defining a vacuum pressure release mechanism for the vacuum extractor.

Embodiment 6: The vacuum extractor of Embodiment 5, wherein the handle does not include any other vacuum release mechanism.

Embodiment 7: The vacuum extractor of any one of Embodiments 1 through 6, wherein an assembly of the grip member and the pump member has a maximum length of 105 mm or less between a proximal end surface of the pump member and a distal end surface of the first laterally extending member of the grip member, a maximum width between a first lateral side surface of the grip member and second lateral side surface of the grip member of 110 mm or less, and a maximum thickness between a front major surface and a rear major surface of the assembly of 20 mm or less.

Embodiment 8: The vacuum extractor of any one of Embodiments 1 through 7, wherein a vacuum pressure of at least −34.6 kPa relative to ambient pressure is achieved within the vacuum cup after moving the pump member from the first position to the second position and then back to the first position five times or less while the vacuum cup is sealed.

Embodiment 9: The vacuum extractor of any one of Embodiments 1 through 8, wherein: one of the grip member and the pump member has surfaces defining a fluid chamber; and another of the grip member and the pump member has surfaces defining a piston disposed and moveable within the fluid chamber in response to movement of the pump member relative to the grip member between the first position and the second position.

Embodiment 10: The vacuum extractor of Embodiment 9, wherein a volume within the fluid chamber is reduced by at least 7.2 cm$^3$ upon movement of the pump member relative to the grip member between the first position and the second position.

Embodiment 11: A vacuum extractor for use in childbirth, comprising: a vacuum cup; a handle coupled to the vacuum cup, the handle including: a grip member; and a pump member movably mounted on the grip member and configured to be manually moved relative to the grip member by a user between a first position and a second position, movement of the pump member relative to the grip member between the first position and the second position generating a vacuum within the vacuum cup when the vacuum cup is disposed on the head of a fetus; wherein an assembly of the grip member and the pump member has a maximum length of 105 mm or less between a proximal end surface of the pump member and a distal end surface of the first laterally extending member of the grip member, a maximum width between a first lateral side surface of the grip member and second lateral side surface of the grip member of 110 mm or less, and a maximum thickness between a front major surface and a rear major surface of the assembly of 20 mm or less, and wherein a vacuum pressure of at least −34.6 kPa relative to ambient pressure is achieved within the vacuum cup after moving the pump member from the first position to the second position and then back to the first position five times or less while the vacuum cup is sealed.

Embodiment 12: A vacuum extractor for use in childbirth, comprising: a vacuum cup; a handle coupled to the vacuum cup, the handle including: a grip member; and a pump member movably mounted on the grip member and configured to be manually moved by a user relative to the grip member between a first position and a second position, movement of the pump member relative to the grip member between the first position and the second position generating a vacuum within the vacuum cup when the vacuum cup is disposed on the head of a fetus; one of the grip member and the pump member having surfaces defining a fluid chamber; and another of the grip member and the pump member having surfaces defining a piston disposed and moveable within the fluid chamber in response to movement of the pump member relative to the grip member between the first position and the second position, wherein an assembly of the grip member and the pump member has a maximum length of 105 mm or less between a proximal end surface of the pump member and a distal end surface of the first laterally extending member of the grip member, a maximum width between a first lateral side surface of the grip member and second lateral side surface of the grip member of 110 mm or less, and a maximum thickness between a front major surface and a rear major surface of the assembly of 20 mm or less; and wherein a volume within the fluid chamber is reduced by at least 7.2 cm$^3$ upon movement of the pump member relative to the grip member between the first position and the second position.

Embodiment 13: A method of forming a vacuum extractor for use in childbirth, comprising: providing a vacuum cup; forming a grip member including a first laterally extending member and a second laterally extending member, the second laterally extending member separated from the first laterally extending member in a longitudinal direction by a distance, wherein each of the first laterally extending member and the second laterally extending member are configured to be gripped by the fingers of a user; forming a handle by moveably mounting a pump member to the grip member and configuring the pump member to be manually movable relative to the grip member by a user between a first position and a second position; coupling the vacuum cup to the handle with a fluid conduit; and configuring the grip member and the pump member such that movement of the pump member relative to the grip member between the first position and the second position generates a vacuum within the vacuum cup when the vacuum cup is disposed on the head of a fetus, wherein the user can grip either the first laterally extending member or the second laterally extending member while pushing the pump member toward the grip member to move the pump member from the first position to the second position during use of the vacuum extractor.

Embodiment 14: The method of Embodiment 13, further comprising forming the first laterally extending member to comprise a generally tubular structure defining a cavity therein, the cavity in fluid communication with an interior of the vacuum cup upon the coupling of the vacuum cup to the handle with the fluid conduit.

Embodiment 15: The method of Embodiment 14, further comprising providing a vacuum pressure indicator extending between an exterior of the grip member and the cavity within the first laterally extending member, and configuring the vacuum pressure indicator to move relative to the first laterally extending member between a first position and a second position, and biasing the vacuum pressure indicator to the first position using a biasing member, and wherein the vacuum pressure indicator is configured to gradually move from the first position toward the second position responsive to increasing vacuum pressure within the cavity, the position of the vacuum pressure indicator relative to the first laterally extending member providing a relative indication of an amount of vacuum pressure within the cavity.

Embodiment 16: The method of Embodiment 15, further comprising providing the vacuum pressure indicator and the first laterally extending member with cooperating features configured to release vacuum pressure within the cavity and the vacuum cup when the vacuum pressure indicator is in the second position relative the first laterally extending member.

Embodiment 17: The method of Embodiment 16, further comprising configuring the vacuum pressure indicator to be manually moveable from the first position to the second position by a user, the vacuum pressure indicator thereby defining a vacuum pressure release mechanism for the vacuum extractor.

Embodiment 18: The method of any one of Embodiments 13 through 17, further comprising forming the grip member and the pump member such that an assembly of the grip member and the pump member has a maximum length of 105 mm or less between a proximal end surface of the pump member and a distal end surface of the first laterally extending member of the grip member, a maximum width between a first lateral side surface of the grip member and second lateral side surface of the grip member of 110 mm or less, and a maximum thickness between a front major surface and a rear major surface of the assembly of 20 mm or less.

Embodiment 19: The method of any one of Embodiments 13 through 18, further comprising configuring the vacuum extractor such that a vacuum pressure of at least −34.6 kPa relative to ambient pressure is achieved within the vacuum cup after moving the pump member from the first position to the second position and then back to the first position five times or less while the vacuum cup is sealed.

Embodiment 20: The method any one of Embodiments 13 through 19, further comprising forming the grip member and the pump member such that: one of the grip member and the pump member has surfaces defining a fluid chamber; and another of the grip member and the pump member has surfaces defining a piston disposed and moveable within the fluid chamber in response to movement of the pump member relative to the grip member between the first position and the second position.

Embodiment 21: The method of Embodiment 20, further comprising forming the grip member and the pump member such that a volume within the fluid chamber is reduced by at least 7.2 cm$^3$ upon movement of the pump member relative to the grip member between the first position and the second position.

The embodiments of the disclosure described above and illustrated in the accompanying drawings do not limit the scope of the disclosure, which is encompassed by the scope of the appended claims and their legal equivalents. Any equivalent embodiments are within the scope of this disclosure. Indeed, various modifications of the disclosure, in addition to those shown and described herein, such as alternate useful combinations of the elements described, will become apparent to those skilled in the art from the description. Such modifications and embodiments also fall within the scope of the appended claims and equivalents.

What is claimed is:

1. A vacuum extractor for use in childbirth, comprising:
a vacuum cup;
a handle coupled to the vacuum cup, the handle including:
   a grip member; and
   a pump member movably mounted on the grip member and configured to be manually moved relative to the grip member by a user between a first position and a second position, movement of the pump member relative to the grip member between the first position and the second position generating a vacuum within the vacuum cup when the vacuum cup is disposed on a head of a fetus;
   wherein the grip member includes a first laterally extending member and a second laterally extending member, the second laterally extending member separated from the first laterally extending member in a longitudinal direction by a distance, wherein each of the first laterally extending member and the second laterally extending member are configured to be gripped by fingers of a user while the pump member is disposed in the palm of the hand of the user, such that the user can grip either the first laterally extending member or the second laterally extending member while pushing the pump member toward the grip member to move the pump member from the first position to the second position during use of the vacuum extractor; and
   wherein a vacuum pressure of at least −34.6 kPa relative to ambient pressure is achieved within the vacuum cup after moving the pump member from the first position to the second position and then back to the first position five times or less while the vacuum cup is sealed.

2. The vacuum extractor of claim 1, wherein the first laterally extending member comprises a generally tubular structure defining a cavity therein, the cavity in fluid communication with an interior of the vacuum cup.

3. The vacuum extractor of claim 2, further comprising a vacuum pressure indicator extending between an exterior of the grip member and the cavity within the first laterally extending member, the vacuum pressure indicator configured to move relative to the first laterally extending member between a first position and a second position, the vacuum pressure indicator being biased to the first position by a biasing member, and wherein the vacuum pressure indicator is configured to gradually move from the first position toward the second position responsive to increasing vacuum pressure within the cavity, a position of the vacuum pressure indicator relative to the first laterally extending member providing a relative indication of an amount of vacuum pressure within the cavity.

4. The vacuum extractor of claim 3, wherein the vacuum pressure indicator and the first laterally extending member have cooperating features configured to release vacuum pressure within the cavity and the vacuum cup when the vacuum pressure indicator is in the second position relative the first laterally extending member.

5. The vacuum extractor of claim 3, wherein the vacuum pressure indicator is manually moveable from the first position to the second position by a user, the vacuum pressure indicator thereby defining a vacuum pressure release mechanism for the vacuum extractor.

6. The vacuum extractor of claim 5, wherein the handle does not include any other vacuum release mechanism.

7. The vacuum extractor of claim 1, wherein an assembly of the grip member and the pump member has a maximum length of 105 mm or less between a proximal end surface of the pump member and a distal end surface of the first laterally extending member of the grip member, a maximum width between a first lateral side surface of the grip member and second lateral side surface of the grip member of 110 mm or less, and a maximum thickness between a front major surface and a rear major surface of the assembly of 20 mm or less.

8. The vacuum extractor of claim 1, wherein:
one of the grip member and the pump member has surfaces defining a fluid chamber; and
another of the grip member and the pump member has surfaces defining a piston disposed and moveable within the fluid chamber in response to movement of the pump member relative to the grip member between the first position and the second position.

9. The vacuum extractor of claim 8, wherein a volume within the fluid chamber is reduced by at least 7.2 cm³ upon movement of the pump member relative to the grip member between the first position and the second position.

10. A vacuum extractor for use in childbirth, comprising:
a vacuum cup;
a handle coupled to the vacuum cup, the handle including:
a grip member; and
a pump member movably mounted on the grip member and configured to be manually moved relative to the grip member by a user between a first position and a second position, movement of the pump member relative to the grip member between the first position and the second position generating a vacuum within the vacuum cup when the vacuum cup is disposed on a head of a fetus;
wherein an assembly of the grip member and the pump member has a maximum length of 105 mm or less between a proximal end surface of the pump member and a distal end surface of a first laterally extending member of the grip member, a maximum width between a first lateral side surface of the grip member and second lateral side surface of the grip member of 110 mm or less, and a maximum thickness between a front major surface and a rear major surface of the assembly of 20 mm or less, and wherein a vacuum pressure of at least −34.6 kPa relative to ambient pressure is achieved within the vacuum cup after moving the pump member from the first position to the second position and then back to the first position five times or less while the vacuum cup is sealed.

11. A vacuum extractor for use in childbirth, comprising:
a vacuum cup;
a handle coupled to the vacuum cup, the handle including:
a grip member; and
a pump member movably mounted on the grip member and configured to be manually moved by a user relative to the grip member between a first position and a second position, movement of the pump member relative to the grip member between the first position and the second position generating a vacuum within the vacuum cup when the vacuum cup is disposed on a head of a fetus;
one of the grip member and the pump member having surfaces defining a fluid chamber; and
another of the grip member and the pump member having surfaces defining a piston disposed and moveable within the fluid chamber in response to movement of the pump member relative to the grip member between the first position and the second position,
wherein an assembly of the grip member and the pump member has a maximum length of 105 mm or less between a proximal end surface of the pump member and a distal end surface of a first laterally extending member of the grip member, a maximum width between a first lateral side surface of the grip member and second lateral side surface of the grip member of 110 mm or less, and a maximum thickness between a front major surface and a rear major surface of the assembly of 20 mm or less; and
wherein a vacuum pressure of at least −34.6 kPa relative to ambient pressure is achieved within the vacuum cup after moving the pump member from the first position to the second position and then back to the first position five times or less while the vacuum cup is sealed.

12. A method of forming a vacuum extractor for use in childbirth, comprising:
providing a vacuum cup;
forming a grip member including a first laterally extending member and a second laterally extending member, the second laterally extending member separated from the first laterally extending member in a longitudinal direction by a distance, wherein each of the first laterally extending member and the second laterally extending member are configured to be gripped by fingers of a user;
forming a handle by moveably mounting a pump member to the grip member and configuring the pump member to be manually movable relative to the grip member by a user between a first position and a second position;
coupling the vacuum cup to the handle with a fluid conduit;

configuring the grip member and the pump member such that movement of the pump member relative to the grip member between the first position and the second position generates a vacuum within the vacuum cup when the vacuum cup is disposed on a head of a fetus, wherein the user can grip either the first laterally extending member or the second laterally extending member while pushing the pump member toward the grip member to move the pump member from the first position to the second position during use of the vacuum extractor; and configuring the vacuum extractor such that a vacuum pressure of at least −34.6 kPa relative to ambient pressure is achieved within the vacuum cup after moving the pump member from the first position to the second position and then back to the first position five times or less while the vacuum cup is sealed.

13. The method of claim 12, further comprising forming the first laterally extending member to comprise a generally tubular structure defining a cavity therein, the cavity in fluid communication with an interior of the vacuum cup upon the coupling of the vacuum cup to the handle with the fluid conduit.

14. The method of claim 13, further comprising providing a vacuum pressure indicator extending between an exterior of the grip member and the cavity within the first laterally extending member, and configuring the vacuum pressure indicator to move relative to the first laterally extending member between a first position and a second position, and biasing the vacuum pressure indicator to the first position using a biasing member, and wherein the vacuum pressure indicator is configured to gradually move from the first position toward the second position responsive to increasing vacuum pressure within the cavity, a position of the vacuum pressure indicator relative to the first laterally extending member providing a relative indication of an amount of vacuum pressure within the cavity.

15. The method of claim 14, further comprising providing the vacuum pressure indicator and the first laterally extending member with cooperating features configured to release vacuum pressure within the cavity and the vacuum cup when the vacuum pressure indicator is in the second position relative the first laterally extending member.

16. The method of claim 15, further comprising configuring the vacuum pressure indicator to be manually moveable from the first position to the second position by a user, the vacuum pressure indicator thereby defining a vacuum pressure release mechanism for the vacuum extractor.

17. The method of claim 12, further comprising forming the grip member and the pump member such that an assembly of the grip member and the pump member has a maximum length of 105 mm or less between a proximal end surface of the pump member and a distal end surface of the first laterally extending member of the grip member, a maximum width between a first lateral side surface of the grip member and second lateral side surface of the grip member of 110 mm or less, and a maximum thickness between a front major surface and a rear major surface of the assembly of 20 mm or less.

18. The method of claim 12, further comprising forming the grip member and the pump member such that:

one of the grip member and the pump member has surfaces defining a fluid chamber; and another of the grip member and the pump member has surfaces defining a piston disposed and moveable within the fluid chamber in response to movement of the pump member relative to the grip member between the first position and the second position.

19. The method of claim 18, further comprising forming the grip member and the pump member such that a volume within the fluid chamber is reduced by at least 7.2 cm$^3$ upon movement of the pump member relative to the grip member between the first position and the second position.

* * * * *